US009114199B2

(12) United States Patent
Richard et al.

(10) Patent No.: US 9,114,199 B2
(45) Date of Patent: *Aug. 25, 2015

(54) IMPLANTABLE OR INSERTABLE MEDICAL DEVICES CONTAINING ACRYLIC COPOLYMER FOR CONTROLLED DELIVERY OF THERAPEUTIC AGENT

(75) Inventors: Robert E. Richard, Wrentham, MA (US); Marlene C. Schwarz, Auburndale, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2719 days.

This patent is subject to a terminal disclaimer.

(21) Appl. No.: 10/632,061

(22) Filed: Jul. 31, 2003

(65) Prior Publication Data

US 2005/0025802 A1  Feb. 3, 2005

(51) Int. Cl.
  *A61L 31/10* (2006.01)
  *A61L 27/34* (2006.01)
  *C08L 53/02* (2006.01)
  *A61L 31/16* (2006.01)
  *A61L 27/54* (2006.01)
  *A61L 29/08* (2006.01)
  *A61L 29/16* (2006.01)

(52) U.S. Cl.
  CPC ............. *A61L 31/16* (2013.01); *A61L 27/34* (2013.01); *A61L 27/54* (2013.01); *A61L 29/085* (2013.01); *A61L 29/16* (2013.01); *A61L 31/10* (2013.01); *A61L 2300/602* (2013.01)

(58) Field of Classification Search
  CPC ....... A61L 31/10; A61L 29/085; A61L 27/34; C08L 53/02
  See application file for complete search history.

(56) References Cited

U.S. PATENT DOCUMENTS

| 4,038,264 | A |   | 7/1977  | Rostoker et al. |           |
|-----------|---|---|---------|-----------------|-----------|
| 4,946,899 | A |   | 8/1990  | Kennedy et al.  | 525/244   |
| 5,258,020 | A |   | 11/1993 | Froix           | 623/1     |
| 5,260,020 | A | * | 11/1993 | Wilk et al.     | 422/22    |
| 5,304,121 | A |   | 4/1994  | Sahatjian       | 604/53    |
| 5,616,608 | A |   | 4/1997  | Kinsella et al. | 514/449   |
| 5,716,981 | A |   | 2/1998  | Hunter et al.   | 514/449   |
| 5,733,925 | A |   | 3/1998  | Kunz et al.     | 514/449   |
| 5,741,331 | A |   | 4/1998  | Pinchuk         | 623/11    |
| 5,837,313 | A | * | 11/1998 | Ding et al.     | 427/2.21  |
| 5,856,367 | A |   | 1/1999  | Barrows et al.  | 521/64    |
| 5,879,697 | A |   | 3/1999  | Ding et al.     | 424/422   |
| 5,954,706 | A |   | 9/1999  | Sahatjian       | 604/509   |
| 6,099,562 | A |   | 8/2000  | Ding et al.     | 623/1.46  |
| 6,110,483 | A |   | 8/2000  | Whitbourne et al. |         |
| 6,187,370 | B1 | * | 2/2001 | Dinh et al.     | 427/2.24  |
| 6,280,411 | B1 |   | 8/2001 | Lennox          | 604/103.05|
| 6,335,029 | B1 |   | 1/2002 | Kamath et al.   | 424/423   |
| 6,514,515 | B1 | * | 2/2003 | Williams        | 424/424   |

| 2002/0045706 | A1 |   | 4/2002  | Houston et al. | 525/100   |
|--------------|----|---|---------|----------------|-----------|
| 2002/0077418 | A1 |   | 6/2002  | Chen et al.    |           |
| 2002/0107330 | A1 | * | 8/2002  | Pinchuk et al. | 525/242   |
| 2003/0138415 | A1 |   | 7/2003  | Shepard        |           |
| 2003/0236514 | A1 | * | 12/2003 | Schwarz        | 604/890.1 |

FOREIGN PATENT DOCUMENTS

| EP | 0 484 057 A2    |   | 5/1992  | ............. A61L 33/00 |
|----|-----------------|---|---------|--------------------------|
| EP | 0484057 A2      |   | 5/1992  |                          |
| WO | WO 00/59968     | * | 10/2000 |                          |
| WO | WO 0061203 A    | * | 10/2000 |                          |
| WO | 01/18079 A1     |   | 3/2001  |                          |
| WO | WO 01/18079 A1  |   | 3/2001  | ............. C08F 220/30 |
| WO | 02/47731 A2     |   | 6/2002  |                          |
| WO | WO 02/47731 A2  |   | 6/2002  |                          |
| WO | 03/032815 A2    |   | 4/2003  |                          |
| WO | WO 03/032815 A2 |   | 4/2003  |                          |
| WO | 03/084583 A2    |   | 10/2003 |                          |
| WO | WO 03/084583 A2 |   | 10/2003 | ............. A61L 31/10 |
| WO | 03/090806 A1    |   | 11/2003 |                          |
| WO | WO 03/090806 A1 |   | 11/2003 | ............. A61L 31/10 |
| WO | 2004/000267 A1  |   | 12/2003 |                          |
| WO | 2004/000380 A1  |   | 12/2003 |                          |
| WO | 2004/000381 A1  |   | 12/2003 |                          |
| WO | 2004/000384 A1  |   | 12/2003 |                          |
| WO | WO 2004/000267 A1 | | 12/2003 | ............. A61K 9/00  |
| WO | WO 2004/000380 A1 | | 12/2003 | ............. A61L 27/34 |
| WO | WO 2004/000381 A1 | | 12/2003 | ............. A61L 27/34 |
| WO | WO 2004/000384 A1 | | 12/2003 | ............. A61L 31/10 |
| WO | 2004/011055 A2  |   | 2/2004  |                          |

(Continued)

OTHER PUBLICATIONS

James F. Beecher et al., "Morphology and Mechanical Behavior of Block Polymers," *J. Polymer Sci. Part C*, No. 26 (1969), pp. 117-134.

Kohtaro Kimishima et al., "Control of Self-Assembled Structures in Binary Mixtures of A-B Diblock Copolymer and A-C Diblock Copolymer by Changing the Interaction between B and C Block Chains," *Macromolecules*, 1999, No. 32, pp. 2585-2596.

Richard J. Spontak et al., "Phase Behavior of Ordered Diblock Copolymer Blends: Effect of Compositional Heterogeneity," *Macromolecules*, 1996, No. 29, pp. 4494-4507.

Hong G. Jeon et al., "Microphase and Macrophase Transitions in Binary Blends of Diblock Copolymers," *Macromolecules*, 1999, No. 32, pp. 1803-1808.

Joseph C. Salamone, ed., *Concise Polymeric Materials Encyclopedia*, Boca Raton (CRC Press, 1999), pp. 812-814.

(Continued)

*Primary Examiner* — Jeffrey S Lundgren
*Assistant Examiner* — Chris Simmons
(74) *Attorney, Agent, or Firm* — Seager, Tufte & Wickhem, LLC

(57) ABSTRACT

Implantable or insertable medical devices are described. The medical devices comprise (a) a therapeutic agent and (b) a polymeric release region, which controls the release of the therapeutic agent upon administration to a patient. The polymeric release region further comprises an acrylic copolymer, which comprises (i) a plurality of rubbery acrylic units and (ii) a plurality of hard units. Also described are methods for administering a therapeutic agent to a patient using the above implantable or insertable medical devices as well as methods of making the above devices.

24 Claims, No Drawings

(56) References Cited

FOREIGN PATENT DOCUMENTS

| WO | WO 2004/011055 A2 | 2/2004 | .............. A61L 31/00 |
|---|---|---|---|
| WO |    2004/050140 A2 | 6/2004 | |
| WO | WO 2004/050140 A2 | 6/2004 | |
| WO |    2004/080397 A2 | 9/2004 | |
| WO | WO 2004/080397 A2 | 9/2004 | |
| WO |    2004/091714 A2 | 10/2004 | |
| WO | WO 2004/091714 A2 | 10/2004 | ............ A61M 36/00 |

OTHER PUBLICATIONS

C. Moinean et al, "Synthesis and Characterization of Poly(methyl metbacrylate)-block-poly(n-butyl acryate)-block-poly(methyl metbacrylate) Copolymers by Two-Step Controlled Radical Polymerization (ATRP) Catalyzed by $NiBr_2$ $(PPh_3)_2$, 1," *Macromolecules,* 1999, No. 32, pp. 8277-8282.

Devon A. Shipp et al., "Water-Borne Block Copolymer Synthesis and a Simple and Effective One-Pot Synthesis of Acrylate-Methacrylate Block Copolymers by Atom Transfer Radical Polymerization," Am. Chem. Soc., Polym. Prep., 1999, vol. 40, pp. 448-449.

Y.K. Chong, "A More Versatile Route to Block Copolymers and Other Polymers of Complex Architecture by Living Radical Polymerization: The RAFT Process," *Macromolecules,* vol. 32, 1999, pp. 2071-2074.

Kathryn L. Beers et al, "Controlled/Living Radical Polymerization in the Undergraduate Laboratories. 1. Using ATRP to Prepare Block and Statistical Copolymers of *n*-Butyl Acrylate and Styrene," vol. 78, No. 4, Apr. 2001, pp. 544-547.

Michael J.Monteiro et al., "Synthesis of Butyl Acrylate-Styrene Block Copolymers in Emulsion by Reversible Addition-Fragmentation Chain Transfer. Effect of Surfacant Migration upon Film Formation," *Journal of Polymer Science:* Part A: Polymer Chemistry, vol. 38, 2000, pp. 4206-4217.

Kelly A. Davis et al., "Preparation of Block Copolymers of Polystyrene and Poly (t-butyl acrylate) of Various Molecular Weights and Architectures by Atom Transfer Radical Polymerization," *Journal of Polymer Science: Part A: Polymer Chemistry,* vol. 38, 2000, pp. 2274-2283.

Karin Tortola et al., "Synthesis of Polystyrene-blockpoly(butyl acrylate) Copolymers Using Nitroxide-Mecliated Living Radical Polymerization in Miniemulsion,"Macromolecular Rapid Communications, vol. 22, No. 12, 2001, pp. 957-961.

Ben Reeves, "Recent Advances in Living Free Radical Polymerization," University of Florida, Nov. 20, 2001, pp. 1-14.

"Diblock and Triblock Copolymers," authorship, publication and date unknown, but published prior to the earliest priority date of the present application.

The Glass Transition, http://www.psic.ws/macrog/tq.htm, downloaded on Feb. 19, 2003.

Immiscible Blend Blends, http://www.pslc.ws/macrog/iblend.htm, downloaded on Aug. 15, 2002.

Reference: Polymer Properties, http://www.signmaaldrich.com/imo/assets/3900/Thermal_Transitions_of_Homopolymers.pdf, downloaded prior to the date of the present application.

Sperling, L. H., Polymeric Multicomponent Materials: an Introduction, John Wiley & Sons, 1997, 284-285.

Lawrence A. Wood, "Glass Transition Temperatures of Copolymers", Journal of Polymer Science, vol. XXVIII, pp. 319-330 (1958).

\* cited by examiner

IMPLANTABLE OR INSERTABLE MEDICAL DEVICES CONTAINING ACRYLIC COPOLYMER FOR CONTROLLED DELIVERY OF THERAPEUTIC AGENT

FIELD OF THE INVENTION

The present invention relates to implantable or insertable medical devices in which acrylic copolymers are used to control delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. Accordingly, there is a continuing need for polymeric materials that can serve as release regions, such as barrier layers and/or carrier layers, which are able to provide a range of therapeutic agent release rates.

SUMMARY OF THE INVENTION

The present invention is directed to novel implantable or insertable medical devices, which provide controlled release of a therapeutic agent.

According to an aspect of the present invention, an implantable or insertable medical device is provided, which comprises: (a) a therapeutic agent and (b) a polymeric release region that controls the release of the therapeutic agent upon administration to a patient. The polymeric release region further comprises an acrylic copolymer, which comprises (i) a plurality of rubbery acrylic units and (ii) a plurality of hard units.

The polymeric release region of the implantable or insertable medical device can be, for example, (a) a carrier region that comprises the therapeutic agent or (b) a barrier region that is disposed over a therapeutic-agent-containing region that comprises the therapeutic agent. In certain embodiments, the polymeric release region is in the form of a coating layer.

Examples of implantable or insertable medical device include catheters, guide wires, balloons, filters, stents, stent grafts, vascular grafts, vascular patches, and shunts. The implantable or insertable medical device may be adapted for implantation or insertion into, for example, the coronary vasculature, peripheral vascular system, esophagus, trachea, colon, biliary tract, urinary tract, prostate or brain.

The therapeutic agent can be selected from any number of categories, including anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

In some embodiments, the acrylic copolymer has an elongation at break of at least 25% at ambient temperature.

Examples of hard units for use the acrylic copolymer include methacrylate ester units and vinyl aromatic units.

In some embodiments, the acrylic copolymer is a block copolymer comprising (a) a rubbery block of the rubbery acrylic units and (b) a hard block of the hard units. The block copolymer can be, for example, a linear copolymer, or a branched copolymer, for instance, having a configuration selected from a star-shaped configuration, a comb configuration and a dendritic configuration. The block copolymer can be, for example, a diblock copolymer, a triblock copolymer, a graft copolymer and so forth.

Examples of rubbery blocks for use in connection with the acrylic block copolymers include poly(alkyl acrylate) blocks such as poly(methyl acrylate) blocks or poly(butyl acrylate) blocks, poly(haloalkyl acrylate) blocks, and poly(cyanoalkyl acrylate) blocks. Examples of hard blocks include poly(vinyl aromatic) blocks, for example, substituted or unsubstituted polystyrene blocks, and poly(methacrylic) blocks, for example, poly(alkyl methacrylate) blocks such as poly(methyl methacrylate) blocks or poly(hydroxyethyl methacrylate) blocks.

In many embodiments, the rubbery block of the block copolymer will correspond to a rubbery phase within the release region at ambient temperatures, and the hard block will correspond to a hard phase within the release layer at ambient temperatures that is distinct from the rubbery phase.

In many embodiments, the above copolymers will comprise (a) a first glass transition temperature that is greater than ambient temperature, for example, greater than 75° C., and (b) a second glass transition temperature that is less than ambient temperature, for example, less than 10° C.

According to another aspect of the present invention, a method of forming the above implantable or insertable medical device is provided. The method comprises (a) providing a solution comprising the acrylic copolymer and a solvent (which can comprise two or more solvent species); and (b) forming the release region from the solution by removing the solvent from the solution. Solvent spraying is one beneficial technique for forming the release region. In some embodiments (for example, where a carrier region is formed), the solution can further comprise the therapeutic agent in dissolved or dispersed form. In other embodiments (for example, where a barrier region is formed), the solution is applied over a therapeutic-agent-containing region.

According to another aspect of the present invention, a method is provided for releasing a therapeutic agent within a patient. The method comprises (a) providing an implantable or insertable medical device like that above, (b) implanting or inserting the therapeutic-agent-releasing medical device of into the patient. In certain embodiments, the medical device is inserted into the vasculature, where the therapeutic agent is released for example, in the treatment of restenosis. Upon implantation or insertion of the device into the patient, the release of the therapeutic agent from the device can correspond, for example, to a sustained release profile.

One advantage of the present invention is that implantable or insertable medical devices can be provided, which provide for controlled release of a therapeutic agent.

Another advantage of the present invention is that implantable or insertable medical devices can be provided, which have release regions containing a variety of materials.

Another advantage of the present invention is that implantable or insertable medical devices can be provided, which are relatively resistant to the effects of radiation sterilization.

These and other embodiments and advantages of the present invention will become immediately apparent to those of ordinary skill in the art upon review of the Detailed Description and Claims to follow.

DETAILED DESCRIPTION OF THE INVENTION

The present invention relates to implantable or insertable medical devices comprising (a) a therapeutic agent and (b) a polymeric release region comprising an acrylic copolymer, which controls the release of the therapeutic agent upon administration to a patient.

The polymeric release region can be provided in a number of configurations. For example, the polymeric release region can constitute the entirety of the medical device, or it can constitute only a portion of the medical device. The portion of the medical device can be, for example, one or more medical device layers (e.g., one or more coating layers), one or medical device components or portions thereof, and so forth.

By "release region" is meant a region that regulates the rate of release of a therapeutic agent. Release regions are commonly either carrier regions or barrier regions. A "carrier region" is a region which contains at least one therapeutic agent and from which the therapeutic agent is released. A "barrier region" is a region that is disposed between a source of therapeutic agent and a site of intended release, which controls the rate at which the therapeutic agent is released.

For instance, in some embodiments of the present invention, an outer carrier layer is disposed over at least a portion of an implantable or insertable medical device. Upon implantation or insertion of the device, the therapeutic agent is released from the carrier layer in a controlled fashion. In other embodiments, a therapeutic-agent-containing layer and a barrier layer are provided over at least a portion of an implantable or insertable medical device. Because the barrier layer is disposed over the therapeutic-agent-containing layer, the barrier layer acts to control release of the therapeutic agent from the medical device upon implantation or insertion of the same.

Release region thickness can be varied to control the release of therapeutic agent. Moreover, multiple release regions can be employed to achieve this end. In addition, where a carrier region is employed, a therapeutic-agent concentration gradient can be established within the carrier region to control release of the therapeutic agent.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent that delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

As previously noted, the polymeric release region of the medical devices of the present invention comprises an acrylic copolymer. A "polymer" is a molecule having one or more chains within which multiple copies of one or more constitutional units are found. A specific example of a polymer is polystyrene

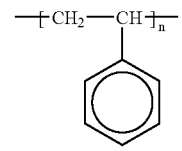

in which n styrene constitutional units are found.

The acrylic copolymers that are used in connection with the present invention contain at least two dissimilar constitutional units. At least one of the dissimilar units is a rubbery acrylic unit. A "rubbery acrylic unit," is a constitutional unit which corresponds to a monomer that can exhibit a glass transition temperature ($T_g$), as measured by any of a number of techniques, including differential scanning calorimetry (DSC), dynamic mechanical analysis (DMA), or dielectric analysis (DEA), that is below ambient temperature when the monomer is in homopolymer form. Moreover, at least one of the dissimilar units is a hard unit. A "hard unit," is a constitutional unit which corresponds to a monomer that can exhibit either (a) a $T_g$ that is above ambient temperature when in homopolymer form or (b) a melting point ($T_m$), as measured by any of a number of techniques including differential scanning calorimetry (DSC), dynamic mechanical analysis (DMA) or dielectric analysis (DEA), that is above ambient temperature when in homopolymer form. Each of the at least two dissimilar constitutional units is typically repeated within the molecule at least 10 times, more typically at least 50, 100 or 500 or more times.

Such acrylic copolymers may contain (a) one or more chains containing repeating constitutional units of a single type (e.g., block copolymers), (b) one or more chains containing randomly distributed constitutional units of two or more types (e.g., random copolymers), (c) one or more chains containing two or more constitutional units that repeat within an ongoing series (e.g., alternating copolymers), and so forth.

The acrylic copolymers of the present invention may be provided in a variety of configurations, including cyclic, linear and branched configurations. Branched configurations include star-shaped configurations (e.g., configurations in which three or more chains emanate from a single branch point), comb configurations (e.g., graft copolymers having a main chain and a plurality of branching side chains), and dendritic configurations (including arborescent or hyper-branched copolymers).

The acrylic copolymers of the present invention typically have an elongation at break of at least 25% at ambient temperature. "Elongation" is an increase in length of a test specimen under tension, stated herein as a percentage of the original length. The "elongation at break" is the amount of elongation that is observed at the point where the specimen breaks or otherwise fails under tension. Ambient temperature is typically 25° C.-45° C., more typically body temperature (e.g., 35° C.-40° C.).

Numerous rubbery acrylic units can be used in connection with the acrylic copolymers of the present invention. For example, the rubbery acrylic units can correspond to the following monomers: alkyl acrylates, haloalkyl acrylates, alkoxyalkyl acrylates and cyanoalkyl acrylates.

Suitable alkyl acrylates, which may contain, for example, linear, branched or cyclic alkyl groups, include the following (which are listed along with a published $T_g$ for the homopolymer): methyl acrylate ($T_g$ 10° C.), ethyl acrylate ($T_g$ −24° C.), propyl acrylate, isopropyl acrylate ($T_g$ −11° C.), butyl acrylate ($T_g$ −54° C.), sec-butyl acrylate ($T_g$ −26° C.), isobutyl acrylate ($T_g$ −24° C.), 2-ethylhexyl acrylate ($T_g$ −50° C.) and dodecyl acrylate ($T_g$ −3° C.).

Suitable haloalkyl acrylates include 2,2,2-trifluoroethyl acrylate ($T_g$ −10° C.).

Suitable cyanoalkyl acrylates include 2-cyanoethyl acrylate ($T_g$ 4° C.) and cyanohexyl acrylate ($T_g$ 19° C.).

Suitable alkoxyalkyl acrylates include 2-methoxyethyl acrylate ($T_g$ −50° C.) and 2-ethoxyethyl acrylate ($T_g$ −50° C.).

Numerous hard units can also be used in connection with the acrylic copolymers of the present invention. The hard units can be those that correspond to, for example, vinyl aromatic monomers, other aromatic monomers, other vinyl monomers, methacrylic monomers, acrylic monomers and alkenes.

Vinyl aromatic monomers are those having aromatic and vinyl moieties and include unsubstituted monomers, vinyl-substituted monomers, and ring-substituted monomers. Suitable vinyl aromatic monomers include the following (listed along with a published homopolymer $T_g$ and, in some instances, a published homopolymer $T_m$): (a) unsubstituted vinyl aromatics, such as atactic styrene ($T_g$ 100° C.), isotactic styrene ($T_{g\,100}$° C.) ($T_m$ 240° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylsytrene ($T_g$ 97° C.), 4-methylsytrene ($T_g$ 97° C.), 2,4-dimethylsytrene ($T_g$ 112° C.), 2,5-dimethylsytrene ($T_g$ 143° C.), 3,5-dimethylsytrene ($T_g$ 104° C.), 2,4,6-trimethylsytrene ($T_g$ 162° C.), and 4-tert-butylstyrene ($T_g$ 127° C.), (ii) ring-alkoxylated vinyl aromatics, such as 4-methoxysytrene ($T_g$ 113° C.) and 4-ethoxysytrene ($T_g$ 86° C.), (iii) ring-halogenated vinyl aromatics such as 2-chlorosytrene ($T_g$ 119° C.), 3-chlorosytrene ($T_g$ 90° C.), 4-chlorosytrene ($T_g$ 110° C.), 2,6-dichlorosytrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Other suitable aromatic monomers include acenaphthalene ($T_g$ 214° C.) and indene ($T_g$ 85° C.).

Other suitable vinyl monomers include the following: (a) vinyl alcohol ($T_g$ 85° C.) ($T_m$ 220° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_m$ 322° C.) ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.) ($T_m$ 320° C.), (d) vinyl halides such as vinyl chloride ($T_g$ 81° C.) ($T_m$ 227° C.) and vinyl fluoride ($T_g$ 40° C.) ($T_m$ 171° C.); (e) alkyl vinyl ethers such as methyl vinyl ether ($T_g$ −31° C.) ($T_m$ 144° C.), propyl vinyl ether ($T_g$ −49° C.) ($T_m$ 76° C.), butyl vinyl ether ($T_g$ −55° C.) ($T_m$ 64° C.), isobutyl vinyl ether ($T_g$ −19° C.) ($T_m$ 165° C.), tert-butyl vinyl ether ($T_g$ 88° C.) ($T_m$ 250° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Suitable methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.) ($T_m$ 200° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic monomers such as methacrylonitrile ($T_g$ 120° C.).

Suitable acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as isopropyl acrylate ($T_g$ −11° C.) ($T_m$ 162° C.), tert-butyl acrylate ($T_g$ 43-107° C.) ($T_m$ 193° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic monomers including acrylonitrile ($T_g$ 125° C.) ($T_m$ 319° C.).

Suitable alkene based monomers include the following: ethylene (HDPE) ($T_g$ −125° C.) ($T_m$ 130° C.), isotactic propylene ($T_g$ −8° C.) ($T_m$ 176° C.), 4-methyl pentene ($T_g$ 29° C.) ($T_m$ 250° C.), 1-octadecene ($T_g$ 55° C.), and tetrafluoroethylene ($T_g$ 117° C.) ($T_m$ 327° C.).

One preferred group of copolymers has (a) an acrylate midblock or main chain, which can be for example, a block of poly(methyl acrylate) or poly(butyl acrylate) having a linear, star or branched configuration, and (b) one or more vinyl aromatic or methacrylate endblocks or side chains, for example, endblocks or side chains of polystyrene or methyl methacrylate.

Two particularly preferred copolymers are: (a) graft copolymers having a polyacrylate main chain and polystyrene side chains, and (b) triblock copolymers having a polyacrylate midblock and polystyrene endblocks. The latter are similar to known polystyrene-polyisobutylene-polystyrene triblock copolymers (SIBS copolymers), such as are described in U.S. patent application 20020107330 entitled "Drug delivery compositions and medical devices containing block copolymer", in that both polymers are thermoplastic elastomers having an elastomeric center block and phase separated, hard polystyrene endblocks.

Implantable or insertable medical devices are typically sterilized by exposure to ethylene oxide or to radiation such as gamma or electron beam radiation. Certain therapeutic agents, however, are unstable under ethylene oxide sterilization conditions. On the other hand, radiation sterilization can lead to chain scission and/or crosslinking of polymers within the medical device, leading to changes in the chemical, physical, and drug-eluting properties of the polymers. For instance, radiation can lead to an unacceptable increase in the surface tack of the material, which can in turn cause defects in the polymer if it is expanded (e.g., when it is in the form of a coating on the surface of an expandable stent or balloon).

Acrylate blocks, while not being completely immune to radiation damage, are believed to be less susceptible to radiation damage than are polyisobutylene blocks, which are known to undergo chain scission during irradiation. Hence, in the polystyrene-polyacrylate-polystyrene triblock copolymer, a material is provided, which has properties that are analogous to SIBS copolymers, while also exhibiting improved immunity to radiation-based changes in polymer properties.

The acrylic copolymers of the present invention can be synthesized using a variety of synthesis schemes. For example, copolymers can be formed using any of a number of polymerization techniques, including chain-growth polymerization techniques such as free-radical polymerization, anionic polymerization, Ziegler-Natta polymerization and metallocene polymerization.

Where block copolymers are formed, polymerization techniques known as "living radical polymerization" or "controlled radical polymerization" can be used. Examples include nitroxide-mediated polymerization (NMP), atom transfer radical polymerization (ATRP), and reversible addition-fragmentation chain transfer (RAFT) polymerization. Each of these techniques is well known.

For example, block copolymers containing poly butyl acrylate have reportedly been synthesized using NMP, ATRP and RAFT polymerization. See Tortosa K., et al., "Synthesis of Polystyrene-block-poly(butyl acrylate) block copolymers using nitroxide-mediated living radical polymerization in miniemulsion," *Macromolecular Rapid Communications*, 2001, Vol. 22, pp. 957-961; K. Davis et al., "Preparation of block copolymers of poly(styrene) and poly(t-butyl acrylate) of various molecular weights and architectures by atom transfer radical polymerization," *J. Polym. Sci., Part A. Polymer Chemistry*, 2000, Vol. 38, No. 12, pp. 2274-2283; K. L. Beers et al., "Controlled/Living Radical Polymerization in the Undergraduate Laboratories. 1. Using ATRP to prepare block and statistical copolymers of n-butyl acrylate and styrene," *Journal of Chemical Education*, April 2001, Vol. 78, No. 4, p. 544; M. J. Monteiro et al., "Synthesis of butyl acrylate-styrene block copolymers in emulsion by reversible addition-fragmentation chain transfer: effect of surfactant migration upon film formation," *J. Polym. Sci., Part A: Polymer Chemistry*, 2000, Vol. 38, pp. 4206-4217.

As other examples, acrylate/methacrylate block copolymers have reportedly been synthesized by ATRP and RAFT polymerization. See D. A. Shipp et al., "Water-borne block copolymer synthesis and a simple and effective one-pot synthesis of acrylate-methacrylate block copolymers by atom transfer radical polymerization," *Am. Chem. Soc., Polym. Prep.*, 1999, Vol. 40, p. 448; Y. K. Chong et al., "A more versatile route to block copolymers and other polymers of complex architecture by living radical polymerization: the RAFT process," *Macromolecules*, March 1999, Vol. 32, No. 6, pp. 2071-2074; G. Moineau et al., "Synthesis and characterization of poly(methyl methacrylate)-block-poly(n-butyl acrylate)-block-poly(methyl methacrylate) copolymers by two-step controlled radical polymerization (ATRP) catalyzed by $NiBr_2(PPH_3)_2$."

Once the acrylic copolymer is obtained, numerous techniques are available for forming the polymeric release regions of the present invention. For example, where the selected copolymer has thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the copolymer prior to thermoplastic processing, producing a therapeutic-agent containing carrier region. If not, then a carrier region can nonetheless be formed by subsequent introduction of therapeutic agent as discussed below.

Polymeric release regions can also be formed using solvent-based techniques in which copolymer is first dissolved in a solvent and the resulting mixture is subsequently used to form the polymeric release region.

Where solvent-based techniques are used, the solvent system that is selected will contain one or more solvent species. The solvent system preferably is a good solvent for the copolymer and, where included, for the therapeutic agent as well. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

Typically, a mixture containing solvent and copolymer is applied to a substrate to form a release region. For example, the substrate can be all or a portion of an implantable or insertable medical device, such as a stent, to which a release layer is applied.

On the other hand, the substrate can also be, for example, a template from which the polymeric release region is removed after solvent elimination. Such template-based techniques are particularly appropriate for forming simple objects such as sheets, tubes, cylinders and so forth, which can be easily removed from a template substrate.

In other techniques, for example, fiber forming techniques, the polymeric release region is formed without the aid of a substrate or template.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be dissolved or dispersed in the copolymer/solvent mixture if desired, and hence co-established with the carrier region. In other embodiments, on the other hand, the therapeutic agent can be dissolved or dispersed within a solvent, and the resulting solution contacted with a polymer region that is previously formed using, for example, one or more of the application techniques described above (e.g., dipping, spraying, etc.).

Barrier layers, on the other hand, are formed over a therapeutic-agent-containing region. In some embodiments, the therapeutic-agent-containing region will comprise one or more polymers, which can be selected, for example, from the polymers listed herein. As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

Where the release region is formed using a solvent-based technique, it is preferably dried after application to remove the solvents. The release region typically further conforms to any underlying surface during the drying process.

The medical devices of the present invention are typically sterilized using conventional processes such as exposure to ethylene oxide or radiation such as gamma or electron beam radiation. Certain therapeutic agents, however, are unstable under ethylene oxide sterilization conditions. In such cases, radiation sterilization is typically used, in which case chain scission and/or crosslinking of the acrylic copolymer is addressed, either by taking into account the chemical and physical property changes that occur or by selecting an acrylic copolymer that is relatively resistant to radiation sterilization.

The release profile associated with the release layer can be modified in a number of ways, including (a) changing the type of rubbery acrylic unit(s) and/or hard unit(s) within the copolymer, (b) changing the ratio of rubbery acrylic unit(s) to hard unit(s) within the copolymer, (c) changing the molecular weight of the copolymer, (d) changing the distribution of the rubbery acrylic and hard units within the copolymer (e.g., a block copolymer vs. a random copolymer vs. an alternating copolymer) and/or (e) changing the configuration of the polymer (e.g., a linear copolymer vs. a branched copolymer).

For example, the release profile of the therapeutic agent can be modified by increasing or decreasing the overall hydrophilicity of the acrylic copolymer (or, viewed conversely, decreasing or increasing the overall hydrophobicity). As a specific example, the hydrophilicity of a block copolymer containing one or more acrylate blocks and one or more polystyrene blocks can be increased by replacing at least some of the polystyrene blocks (which are substantially hydrophobic) with blocks of a substantially hydrophilic material such as poly(1-vinyl-2-pyrrolidone). As another example, the hydrophilicity of a copolymer in accordance with the present invention can be increased by incorporating hydrophilic monomers such as acrylic acid, methacrylic acid, acrylamide, methacrylamide, and so forth.

The release profile associated with the release layer can also be modified by blending one or more supplementary polymers with the acrylic copolymer within the release layer, or by providing a separate barrier layer that contains one or more supplementary polymers. For example, supplementary polymer(s) can be selected and added to the release layer to vary the overall hydrophilicity of the same.

The supplementary polymers may be, for example, homopolymers or copolymers, crosslinked or uncrosslinked, linear or branched, natural or synthetic, thermoplastic or thermosetting. Supplementary polymers include the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Medical devices having a sustained release profile are preferred in many cases. By "sustained release profile" is meant a release profile in which less than 25% of the total release from the medical device that occurs over the course of implantation/insertion in the body occurs within the first 1, 2, 3 or even more days of administration. Conversely, this means that more than 75% of the total release from the medical device will occur after the device has been implanted/inserted for the same period.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o)agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (i.e., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) a therapeutic agent and (b) a polymeric release region that controls the release of said therapeutic agent upon administration to a patient, said polymeric release region comprising an acrylic graft copolymer which is a block copolymer comprising (i) a rubbery block of rubbery acrylic units and (ii) a hard block of hard units.

2. The implantable or insertable medical device of claim 1, wherein said polymeric release region is a carrier region that comprises said therapeutic agent.

3. The implantable or insertable medical device of claim 1, wherein said polymeric release region is a barrier region disposed over a therapeutic-agent-containing region that comprises said therapeutic agent.

4. The implantable or insertable medical device of claim 1, wherein said polymeric release region is in the form of a coating layer on the medical device.

5. The implantable or insertable medical device of claim 1, wherein said implantable or insertable medical device is selected from a catheter, a guide wire, a balloon, a filter, a stent, a stent graft, a vascular graft, a vascular patch and a shunt.

6. The implantable or insertable medical device of claim 1, wherein said implantable or insertable medical device is adapted for implantation or insertion into the coronary vasculature, peripheral vascular system, esophagus, trachea, colon, biliary tract, urinary tract, prostate or brain.

7. The implantable or insertable medical device of claim 1, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

8. The implantable or insertable medical device of claim 1, wherein said acrylic copolymer has an elongation at break of at least 25% at ambient temperature.

9. The implantable or insertable medical device of claim 1, wherein said hard units are selected from methacrylate ester units and vinyl aromatic units.

10. The implantable or insertable medical device of claim 1, wherein said copolymer is a linear copolymer.

11. The implantable or insertable medical device of claim 1, wherein said copolymer is a branched copolymer having a configuration selected from a star-shaped configuration, a comb configuration and a dendritic configuration.

12. The implantable or insertable medical device of claim 1, wherein said rubbery block is selected from a poly(alkyl acrylate) block, a poly(haloalkyl acrylate) block, and a poly(cyanoalkyl acrylate) block.

13. An implantable or insertable medical device comprising (a) a therapeutic agent and (b) a polymeric release region that controls the release of said therapeutic agent upon administration to a patient, said polymeric release region comprising an acrylic graft copolymer which is a block copolymer comprising (i) a rubbery block of rubbery acrylic units and (ii) a hard block of hard units, wherein said rubbery block is a poly(alkyl acrylate) block selected from a poly(methyl acrylate) block and a poly(butyl acrylate) block.

14. The implantable or insertable medical device of claim 1, wherein said hard block is a poly(vinyl aromatic) block.

15. The implantable or insertable medical device of claim 14, wherein said poly(vinyl aromatic) block is a substituted or unsubstituted polystyrene block.

16. The implantable or insertable medical device of claim 1, wherein said hard block is a poly(methacrylic) block.

17. The implantable or insertable medical device of claim 16, wherein said poly(methacrylic) block is a poly(alkyl methacrylate) block.

18. The implantable or insertable medical device of claim 17, wherein said poly(alkyl methacrylate) block is selected from a poly(methyl methacrylate) block and a poly(hydroxyethyl methacrylate) block.

19. The implantable or insertable medical device of claim 1, wherein said block copolymer is selected from a diblock copolymer and a triblock copolymer.

20. The implantable or insertable medical device of claim 1, wherein said block copolymer comprises a first glass transition temperature that is greater than 75° C. and a second glass transition temperature that is less than 10° C.

21. The implantable or insertable medical device of claim 1, wherein said rubbery block corresponds to a rubbery phase within said release region at ambient temperatures, wherein said hard block corresponds to a hard phase within said release layer at ambient temperatures that is distinct from said rubbery phase.

22. The implantable or insertable medical device of claim 1, wherein said copolymer comprises (a) a first glass transition temperature that is greater than ambient temperature and (b) a second glass transition temperature that is less than ambient temperature.

23. The implantable or insertable medical device of claim 1, wherein said polymeric release region further comprises a supplemental polymer.

24. The implantable or insertable medical device of claim 1, wherein said medical device is sterilized using a quantity of radiation effective to kill pathogens.

* * * * *